US010152789B2

(12) United States Patent
Carnes et al.

(10) Patent No.: US 10,152,789 B2
(45) Date of Patent: Dec. 11, 2018

(54) AUGMENTED SURGICAL REALITY ENVIRONMENT

(71) Applicant: Covidien LP, Mansfield, MA (US)

(72) Inventors: Tony Carnes, Gainesville, FL (US); Edward McKenna, Boulder, CO (US); Stephen Pack, Louisville, CO (US)

(73) Assignee: Covidien LP, Mansfield, MA (US)

( * ) Notice: Subject to any disclaimer, the term of this patent is extended or adjusted under 35 U.S.C. 154(b) by 84 days.

(21) Appl. No.: 15/327,058

(22) PCT Filed: Jul. 20, 2015

(86) PCT No.: PCT/US2015/041083
§ 371 (c)(1),
(2) Date: Jan. 18, 2017

(87) PCT Pub. No.: WO2016/014384
PCT Pub. Date: Jan. 28, 2016

(65) Prior Publication Data
US 2017/0161893 A1   Jun. 8, 2017

Related U.S. Application Data

(60) Provisional application No. 62/028,974, filed on Jul. 25, 2014.

(51) Int. Cl.
*G06T 7/00* (2017.01)
*H04N 5/232* (2006.01)
(Continued)

(52) U.S. Cl.
CPC ............ *G06T 7/0012* (2013.01); *A61B 90/37* (2016.02); *G06T 5/10* (2013.01); *G06T 7/13* (2017.01);
(Continued)

(58) Field of Classification Search
CPC .................................................. G06T 7/0012
See application file for complete search history.

(56) References Cited

U.S. PATENT DOCUMENTS 7,317,841 B2   1/2008   Yatsenko et al.
7,542,622 B1   6/2009   Angelini et al.
(Continued)

OTHER PUBLICATIONS

McLeod A Jonathan et al: "Motion magnification for endoscopic surgery", Progress in Biomedical Optics and Imaging, SPIE—International Society for Optical Engineering, Bellingham, WA, US; vol. 9036, Mar. 12, 2014 (Mar. 12, 2014); pp. 90360C-90360C.
(Continued)

*Primary Examiner* — James Pontius

(57) ABSTRACT

The present disclosure is directed to an augmented reality surgical system for viewing an augmented image of a region of interest during a surgical procedure. The system includes an image capture device that captures an image of the region of interest. A controller receives the image and applies at least one image processing filter to the image. The image processing filter includes a spatial decomposition filter that decomposes the image into spatial frequency bands. A temporal filter is applied to the spatial frequency bands to generate temporally filtered bands. An adder adds each band spatial frequency band to a corresponding temporally filtered band to generate augmented bands. A reconstruction filter generates an augmented image by collapsing the augmented bands. A display displays the augmented image to a user.

20 Claims, 7 Drawing Sheets

(51) Int. Cl.
*G06T 11/00* (2006.01)
*G06T 5/10* (2006.01)
*G06T 19/00* (2011.01)
*G06T 19/20* (2011.01)
*G06T 7/13* (2017.01)
*H04N 5/33* (2006.01)
*A61B 90/00* (2016.01)

(52) U.S. Cl.
CPC .......... *G06T 11/008* (2013.01); *G06T 19/006* (2013.01); *G06T 19/20* (2013.01); *H04N 5/232* (2013.01); *H04N 5/33* (2013.01); *A61B 2090/365* (2016.02); *A61B 2576/00* (2013.01); *G06T 2207/20024* (2013.01); *G06T 2207/30004* (2013.01)

(56) References Cited

U.S. PATENT DOCUMENTS

| | | | |
|---|---|---|---|
| 8,224,425 | B2 | 7/2012 | Freeman et al. |
| 9,591,968 | B2 * | 3/2017 | Gross .................... H04W 76/10 |
| 9,750,420 | B1 * | 9/2017 | Agrawal ............ A61B 5/02427 |
| 2009/0268010 | A1 | 10/2009 | Zhao et al. |
| 2012/0183196 | A1 | 7/2012 | Dasgupta et al. |
| 2013/0038707 | A1 | 2/2013 | Cunningham et al. |
| 2013/0176411 | A1 | 7/2013 | Igarashi et al. |
| 2014/0072190 | A1 * | 3/2014 | Wu ...................... G06T 7/0012 382/128 |
| 2015/0257653 | A1 * | 9/2015 | Hyde ..................... A61B 5/021 600/473 |
| 2016/0035084 | A1 * | 2/2016 | Khachaturian ........ A61B 5/742 382/128 |
| 2016/0252650 | A1 * | 9/2016 | Hirst, Sr. ............... G01V 9/007 348/143 |

OTHER PUBLICATIONS

Hao-Yu Wu et al: "Eulerian video magnification for revealing subtle changes in the world", ACM Transactions on Graphics, vol. 31, No. 4, Jul. 1, 2012 (Jul. 1, 2012); pp. 1-8.

Alexandre Lima et al: "Near-infrared spectroscopy for monitoring peripheral tissue perfusion in critically ill patients", Revista Brasileira de Terapia Intensiva, Sep. 1, 2011 (Sep. 1, 2011); pp. 341-351.

Zoltan Szabo et al: "Real-time intraoperative visualization of myocardial circulation using augmented reality temperature display", International Journal of Cardiovascular Imaging, vol. 29, No. 2, Feb. 1, 2013 (Feb. 1, 2013); pp. 521-528.

Guolan Lu et al: "Medical hyperspectral imaging: a review", International Society for Optical Engineering, vol. 19, No. 1, Jan. 20, 2014 (Jan. 20, 2014); pp. 1-23.

Extended European Search Report corresponding to counterpart European Patent Appln. No. EP 15 82 5456.5 dated Feb. 7, 2018.

Extended European Search Report corresponding to counterpart Patent Appln. No. EP 15824688A dated Feb. 28, 2018.

International Search Report for (PCT/US2015/041083) date of completion is Apr. 29, 2016 (3 pages).

* cited by examiner

AUGMENTED SURGICAL REALITY ENVIRONMENT

CROSS REFERENCE TO RELATED APPLICATIONS

This application is a U.S. National Stage Application filed under 35 U.S.C. § 371(a) of International Patent Application No. PCT/US2015/041083, filed Jul. 20, 2015, which claims the benefit to U.S. Provisional Patent Application No. 62/028,974, filed Jul. 25, 2014, the entire disclosure of each of which is incorporated by reference herein.

BACKGROUND

1. Technical Field

The present disclosure relates to surgical techniques to improve surgical outcomes for a patient. More specifically, the present disclosure is directed to systems and methods for augmenting and enhancing a clinician's field of vision while performing a surgical technique.

2. Background of the Related Art

Minimally invasive surgeries have involved the use of multiple small incisions to perform a surgical procedure instead of one larger opening. The small incisions have reduced patient discomfort and improved recovery times. The small incisions have also limited the visibility of internal organs, tissue, and other matter.

Endoscopes have been inserted in one or more of the incisions to make it easier for clinicians to see internal organs, tissue, and other matter inside the body during surgery. These endoscopes have included a camera with an optical and/or digital zoom capability that is coupled to a display showing the magnified view of organs, tissue, and matter inside the body as captured by the camera. Existing endoscopes and displays, especially those used in surgical robotic systems, have had a limited ability to identify conditions or objects that are within the field of view of the camera but are not fully visible within the spectrum shown on the display.

For example, existing minimally invasive and robotic surgical tools, including but not limited to endoscopes and displays, have had a limited, if any, ability to identify tissue perfusion after resection, locate different sized arteries within tissue, measure the effectiveness of vessel sealing, identify diseased or dead tissue from a heat signature, verify appropriate functioning after a resection, distinguish between sensitive areas (such as the ureter) and surrounding matter (such as surrounding blood), and detecting super-small leaks that are not visible with current tests. In some surgeries these checks were either not performed or more invasive and/or time consuming tests were performed to check for these and other conditions and objects.

There is a need for identifying a greater range of possible conditions or objects that are within the field of view of a surgical camera but are not fully visible within the spectrum shown on the display during surgery.

SUMMARY

In an aspect of the present disclosure, an augmented reality surgical system for viewing an augmented image of a region of interest during a surgical procedure is provided. The system includes an image capture device configured to capture an image of the region of interest. The system also includes a controller configured to receive the image and apply at least one image processing filter to the image to generate an augmented image. The image processing filter includes a spatial decomposition filter configured to decompose the image into a plurality of spatial frequency bands, a temporal filter that is configured to be applied to the plurality of spatial frequency bands to generate a plurality of temporally filtered bands, an adder configured to add each band in the plurality of spatial frequency bands to a corresponding band in the plurality of temporally filtered bands to generate a plurality of augmented bands, and a reconstruction filter configured to generate an augmented image by collapsing the plurality of augmented bands. The augmented image is then displayed to a user.

The image capture device may capture a video having a plurality of image frames and the controller applies the at least one image processing filter to each image frame of the plurality of image frames.

The temporal filter isolates at least one spatial frequency band from the plurality of spatial frequency bands to generate the plurality of temporally filtered bands. The plurality of temporally filtered bands are amplified by an amplifier before each band in the plurality of spatial frequency bands is added to a corresponding band in the plurality of temporally filtered bands to generate a plurality of augmented bands.

The image processing filter may use an edge detection algorithm configured to highlight one or more edges in the image, wherein the one or more highlighted edges is added to the augmented image.

The system may include at least one hyper-spectral sensor configured to obtain a plurality of hyper-spectral images. The image processing filter uses a hyper-spectral algorithm to combine the plurality of spectral images to generate a three dimensional hyper-spectral image cube that is added to the augmented image.

The system may also include an infrared camera configured capture at least one image, wherein the image processing filter generates an infrared image that is added to the augmented image.

In another aspect of the present disclosure, methods for generating an augmented image are provided. A non-transitory computer readable medium, including but not limited to flash memory, compact discs, and solid state drives, may store instructions that, when executed by a processing device, including but not limited to a controller or central processing unit, cause the processing device to perform one or more functions, including the methods described herein. A method may include capturing at least one image using an image capture device. The at least one image is decomposed to generate a plurality of spatial frequency bands. A temporal filter is applied to the plurality of spatial frequency bands to generate a plurality of temporally filtered bands. Each band in the plurality of spatial frequency bands is added to a corresponding band in the plurality of temporally filtered bands to generate a plurality of augmented bands. The plurality of augmented bands is collapsed to generate an augmented image which is displayed on a display.

At least one spatial frequency band is isolated from the plurality of spatial frequency bands. The temporally filtered bands may be amplified before adding each band in the plurality of spatial frequency bands to a corresponding band in the plurality of temporally filtered bands to generate a plurality of augmented bands.

An edge detection algorithm may be applied to highlight one or more edges in the image and the one or more highlighted edges is added to the augmented image.

A plurality of hyper-spectral images may be obtained. The plurality of hyper-spectral images are combined to generate a three dimensional hyper-spectral image cube. The three dimensional hyper-spectral image cube is added to the augmented image.

An infrared image may be obtained and added to the augmented image.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Figure 1:
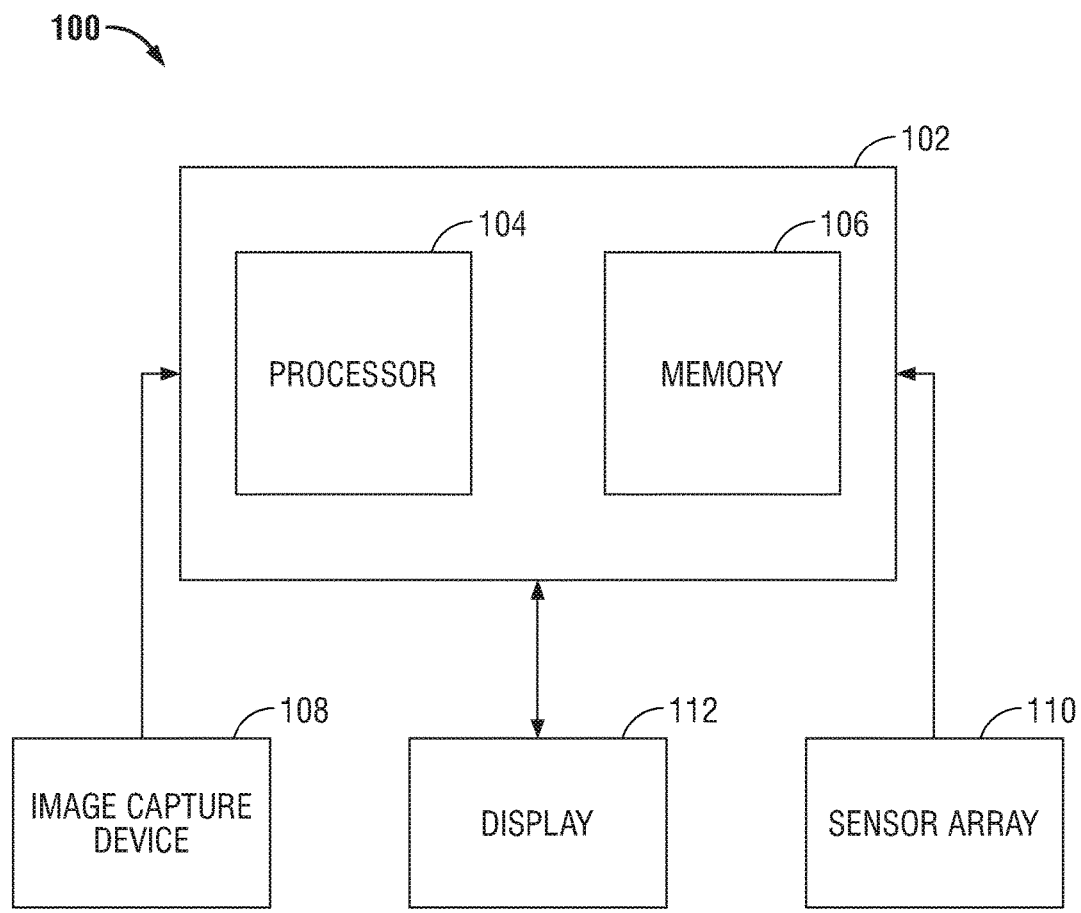
FIG. 1 is a block diagram of a system for augmenting a surgical environment.

Image data captured from a surgical camera during a surgical procedure may be analyzed to identify additional imperceptible properties of objects within the camera field of view that may be invisible or visible but difficult to clearly see for people viewing the camera image displayed on a screen. Various image processing technologies may be applied to this image data to identify different conditions in the patient. For example, Eulerian image amplification techniques may be used to identify wavelength or "color" changes of light in different parts of a capture image. These changes may be further analyzed to identify re-perfusion, arterial flow, and/or vessel types.

Eulerian image amplification may also be used to make motion or movement between image frames more visible to a clinician. In some instances changes in a measured intensity of predetermined wavelengths of light between different image frames may be presented to a clinician to make the clinician more aware of the motion of particular objects of interest (such as blood).

Image algebra may be used to identify an optimal location for cutting tissue or other matter during the surgical procedure. In some instances, image algebra may include edge detection and/or Eulerian image amplification to identify optimal cutting locations.

Hyper-spectral image analysis may be used to identify subtle changes in small areas within the range of view that may be invisible or otherwise difficult for the human eye to discern. These hyper-spectral image analysis techniques may be combined with Eulerian image amplification to identify a specific set of changes in these areas.

Image algebra may be combined with hyper-spectral image analysis to identify an edge of an object or other mass. Image algebra may include edge detection and/or may be combined with both hyper-spectral image analysis and Eulerian image amplification to identify an edge of a mass.

Infrared light may be used to identify a boundary of diseased, dead, and/or abnormal tissue. A filter may be used to isolate one or more desired wavelengths in an infrared, near infrared, or other range from captured image data. Eulerian image amplification and/or image algebra may be used to analyze the filtered image data and identify a particular tissue boundary.

One or more of Eulerian image amplification, image algebra, hyper-spectral image analysis, and filtering technologies may be included as part of an imaging system. These technologies may enable the imaging system to provide additional information about unapparent conditions and objects within a camera's field of view and enhance surgical outcomes. This additional information may include, but is not limited to, identifying tissue perfusion, locating arteries of specific sizes (such as larger arteries), verifying an effectiveness of vessel sealing, identifying a heat signature of abnormal tissue, verifying desired object motion (such as a lack of movement in edges of dead tissue or verifying proper flow after resection), distinguishing between similar looking objects (such as between the ureter, inferior mesenteric artery, and/or surrounding blood), and detecting small leaks (such as leaks that may occur after an anastomosis).

One or more of these technologies may be included as part of an imaging system in a surgical robotic system to provide a clinician with additional information in real time about unapparent conditions and objects within an endoscope's field of view. This may enable the clinician to quickly identify, avoid, and/or correct undesirable situations and conditions during surgery. For example, a clinician may be able to verify during surgery that vessels have been properly sealed, that blood is properly flowing, that there are no air leaks after an anastomosis, and/or that diseased tissue has been removed. The clinician may then be able to correct these issues if needed during the surgery. A clinician may also be able to identify delicate or critical objects in the body that the surgical instruments should avoid contacting or handle extra carefully, such as larger arteries or the ureter.

The present disclosure is directed to systems and methods for providing an augmented image in real time to a clinician during a surgical procedure. The systems and methods described herein apply image processing filters to a captured image to provide an augmented or enhanced image to a clinician via a display. In some embodiments, the systems and methods permit video capture during a surgical procedure. The captured video is processed in real time or near real time and then displayed to the clinician as an augmented image. The image processing filters are applied to each frame of the captured video. Providing the augmented image or video to the clinician permits the clinician to identify and address potential adverse physiologic conditions thereby reducing the need for additional surgical procedures as well as ensuring the effectiveness of the original surgical procedure.

The embodiments described herein enable a clinician to identify areas receiving excessive or ineffective blood, effectiveness of stapling or sealing, temperature variations in organs to identify diseased tissue, subtle tissue movement to determine if tissue is alive, and tissue thickness. Additionally, the embodiments described herein may be used to identify tissue perfusion after resection, location of arteries, distinguish between different tissues, and determine air leaks.

Turning to FIG. 1, a system for augmenting a surgical environment, according to embodiments of the present disclosure, is shown generally as 100. System 100 includes a controller 102 that has a processor 104 and a memory 106. The system 100 also includes an image capture device 108, e.g., a camera, that records still frame images or moving images. A sensor array 110 provides information concerning the surgical environment to the controller 102. For instance, sensor array 110 includes biometric sensors capable of obtaining biometric data of a patient such as, pulse, temperature, blood pressure, blood oxygen levels, heart rhythm, etc. Sensor array 110 may also include hyper-spectral sensors to perform hyper-spectral imaging. A display 112, displays augmented images to a clinician during a surgical procedure. In some embodiments, the controller 102 may communicate with a central server (not shown) via a wireless or wired connection. The central server may store images of a patient or multiple patients that may be obtained using x-ray, a computed tomography scan, or magnetic resonance imaging.

Figure 2A:
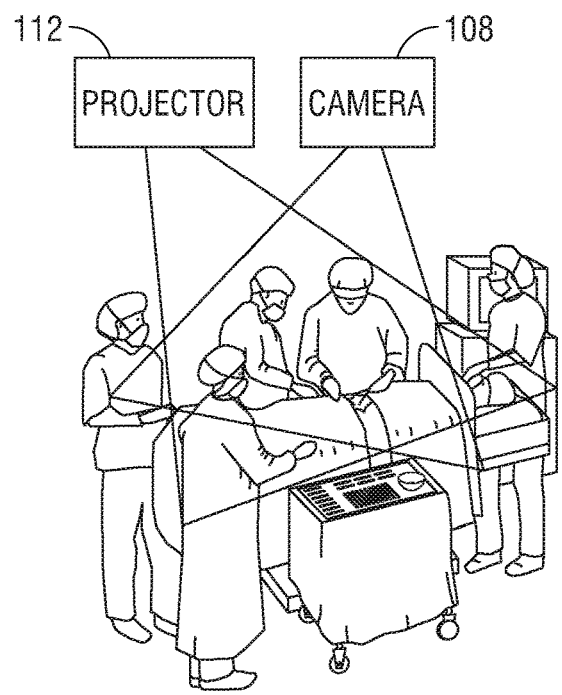
FIGS. 2A-2D are examples of how the system of FIG. 1 may be implemented.
Figure 2B:
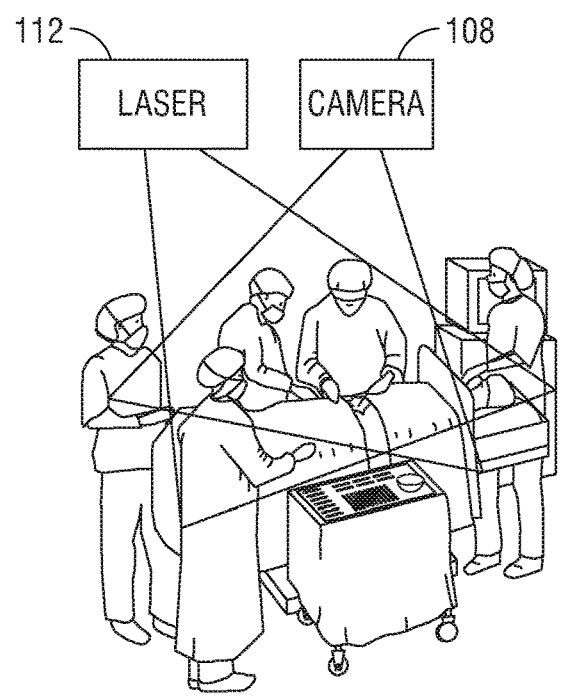
Figure 2C:
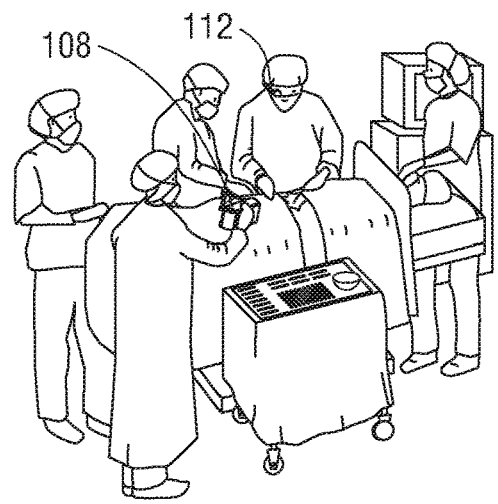
Figure 2D:
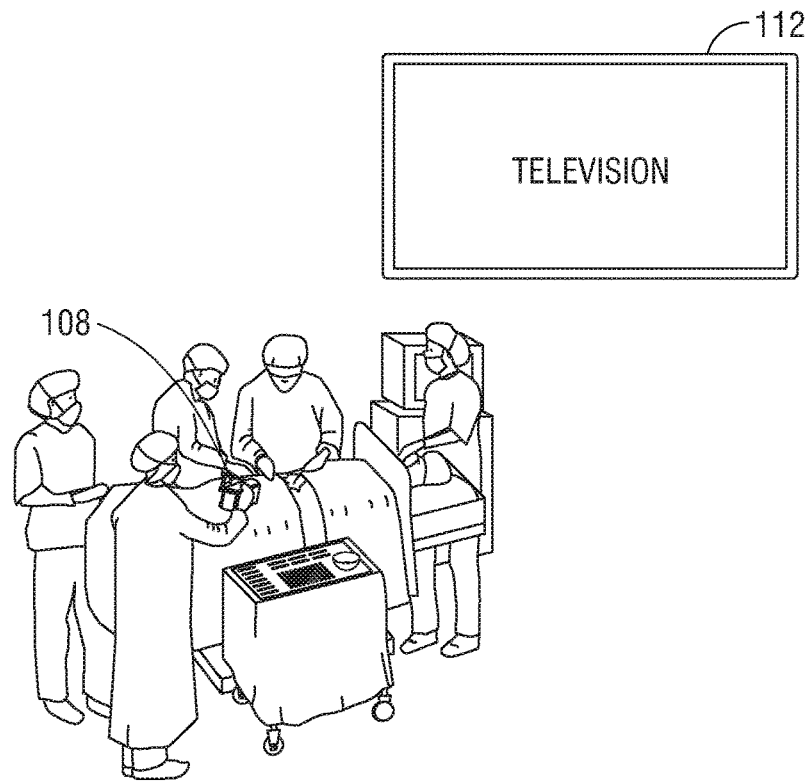

FIGS. 2A-2D depict examples of how the system of FIG. 1 is implemented in a surgical environment. As shown in FIGS. 2A-2D, an image capture device 108 captures images of a surgical environment during a surgical procedure. Images recorded by the image capture device 108, data from the sensor array 110, and images from central server (not shown) are combined by the controller 102 to generate an augmented image that is provided to a clinician via display 112. As shown in FIGS. 2A-2D, display 112 may be a projector (FIG. 2A), a laser projection system (FIG. 2B), a pair of glasses that projects an image onto one of the lenses such as GOOGLE GLASS® (provided by Google®) (FIG. 2C), both lenses, or on a facial shield, or a monitor (FIG. 2D). When using a monitor as shown in FIG. 2D, the augmented image is overlaid on an image of the patient obtained by the image capture device 108.

Figure 3:
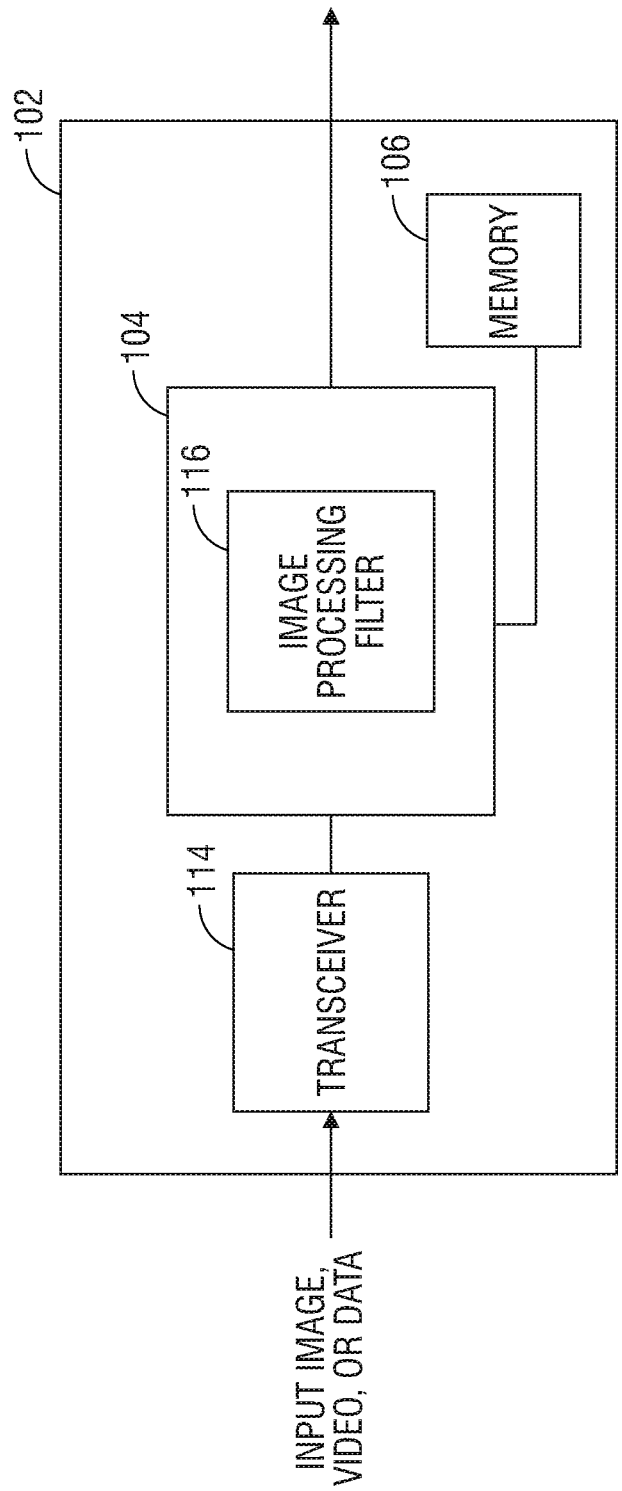
FIG. 3 is a system block diagram of the controller of FIG. 1.

FIG. 3 depicts a system block diagram of the controller 102. As shown in FIG. 3, the controller 102 includes a transceiver 114 configured to receive still frame images or video from the image capture device 108 or data from sensor array 110. In some embodiments, the transceiver 114 may include an antenna to receive the still frame images, video, or data via a wireless communication protocol. The still frame images, video, or data are provided to the processor 104. The processor 104 includes an image processing filter 116 that processes the received still frame images, video, or data to generate an augmented image or video. The image processing filter 116 may be implemented using discrete components, software, or a combination thereof. The augmented image or video is provided to the display 112.

Figure 4:
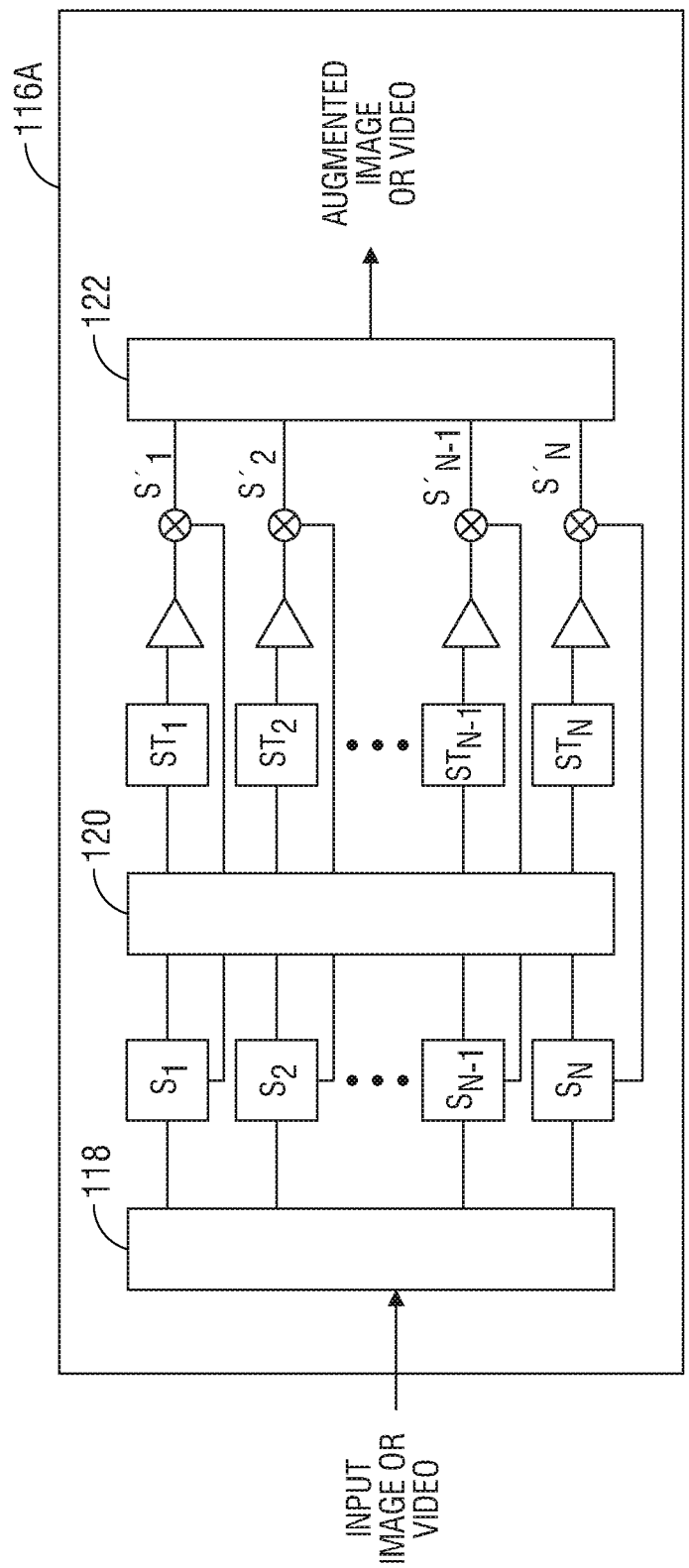
FIG. 4 is a first block diagram of a system for augmenting an image or video.

Turning to FIG. 4, a system block diagram of an image processing filter that may be applied to video received by transceiver 114 is shown as 116A. In the image processing filter 116A, each frame of a received video is decomposed into different spatial frequency bands $S_1$ to $S_N$ using a spatial decomposition filter 118. The spatial decomposition filter 118 uses an image processing technique known as a pyramid in which an image is subjected to repeated smoothing and subsampling.

After the frame is subjected to the spatial decomposition filter 118, a temporal filter 120 is applied to all the spatial frequency bands $S_1$ to $S_N$ to generate temporally filtered bands $ST_1$ to $ST_N$. The temporal filter 120 is a bandpass filter that is used to extract one or more desired frequency bands. For example, if the clinician knows the patient's pulse, the clinician can set the bandpass frequency of the temporal filter 120, using a user interface (not shown), to magnify the spatial frequency band that corresponds to the patient's pulse. In other words, the bandpass filter is set to a narrow range that includes the patient's pulse and applied to all the spatial frequency bands $S_1$ to $S_N$. Only the spatial frequency band that corresponds to the set range of the bandpass filter will be isolated or passed through. All of the temporally filtered bands $ST_1$ to $ST_N$ are individually amplified by an amplifier having a gain a. Because the temporal filter isolates or passes through a desired spatial frequency band, only the desired spatial frequency band gets amplified. The amplified temporally filtered bands $ST_1$ to $ST_N$ are then added to the original spatial frequency bands $S_1$ to $S_N$ to generate augmented bands $S'_1$ to $S'_N$. Each frame of the video is then reconstructed using a reconstruction filter 122 by collapsing augmented bands $S'_1$ to $S'_N$ to generate an augmented frame. All the augmented frames are combined to produce the augmented video. The augmented video that is shown to the clinician includes a portion that is magnified, i.e., the portion that corresponds the desired spatial frequency band, to enable the clinician to easily identify such portion.

In some embodiments, instead of using an amplifier to amplify the isolated temporally filtered band, the image processing filter 116A may highlight the temporally filtered band using a one or more colors before reconstructing the video. Using a different color for a desired portion of the patient, e.g., a vessel or nerve, may make it easier for the clinician to identify the location of such portion.

Figure 5:
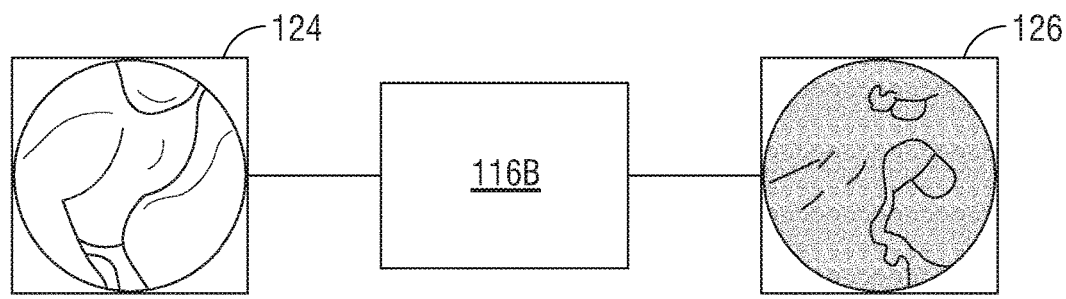
FIG. 5 is a second block diagram of a system for augmenting an image or video.

Turning to FIG. 5, a system block diagram of an image processing filter that may be applied to a still frame image or video received by transceiver 114 is shown as 116B. As shown in FIG. 5, an input image 124 (i.e., a captured image or a frame from a video) is inputted into image processing filter 116B. The image processing filter 116B then employs an edge detection algorithm on the inputted image 124 and outputs a filtered image 126 that highlights the edges found in the input image 124.

Figure 6:
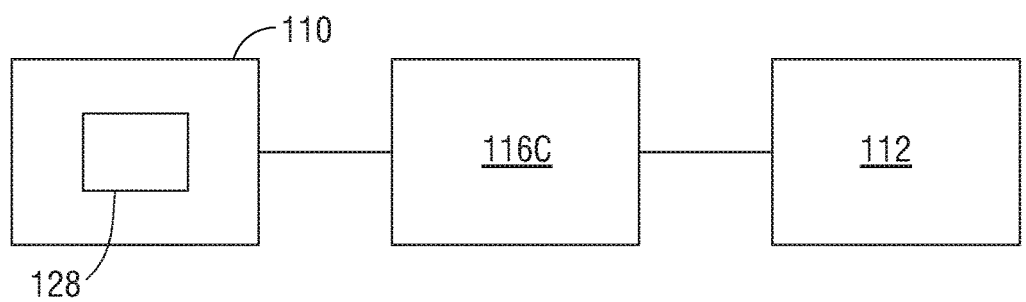
FIG. 6 is a third block diagram of a system for augmenting an image or video.

FIG. 6 depicts a block diagram of a system for generating a hyper-spectral image. As shown in FIG. 6, sensor array 110 includes hyper-spectral sensors 128. The hyper-spectral sensors 128 collect a set of images where each image represents a different range of the electromagnetic spectrum. The set of images are sent to image processing filter 116C which employs an hyper-spectral algorithm to combine the set of images to form a three-dimensional (3D) hyper-spectral image cube. The 3D hyper-spectral image cube is outputted to the display 112

Figure 7:
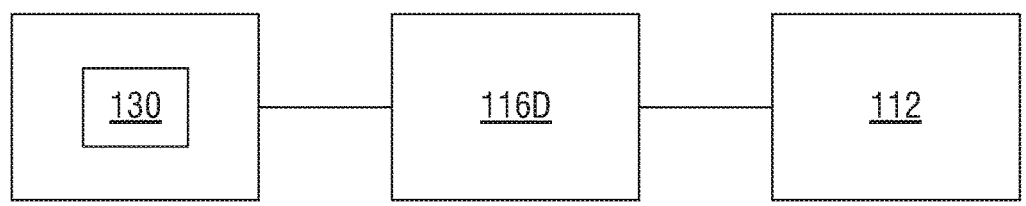
FIG. 7 is a fourth block diagram of a system for augmenting an image or video.

FIG. 7 depicts a block diagram of a system for generating an infrared image. As shown in FIG. 7, an infrared camera 130 captures images or video and transmits the captured images or video to image processing filter 116D. Image processing filter 116D processes the received captured images or video to generate an infrared image that is displayed on display 112.

The image processing filters described above, i.e., 116A-116D, may be used individually to identify physical conditions during a surgical procedure. In some embodiments, image processing filter 116A may be used to identify changes in color in order to identify tissue perfusion or re-perfusion after a resection, arterial flow, vessel types. Image processing filter 116A may also be used to enhance visibility of motion identify edges of necrotic tissue or appropriate functioning of tissue after resection.

In some embodiments, the above-described filters may be combined to assist the clinician in identifying adverse physical conditions. For instance, image processing filters 116A and 116B may be combined to identify edges of different tissues to determine the most effective placement for performing a task, e.g., cutting. Image processing filters 116A and 116C may be combined to identify subtle changes in small areas, e.g., air leaks that cannot be determined by conventional methods. Image processing filters 116A, 116B, and 116C may be combined to identify edges of a mass, e.g., a tumor. Image processing filters 116A, 116B, and 116D may be combined to identify the boundary of diseased tissue.

Image processing filters 116A, 116, B, 116C, and 116D may be implemented using different circuits or they may be implemented using a single processor that executes different subroutines based on the filter that is applied to the image.

Figure 8:
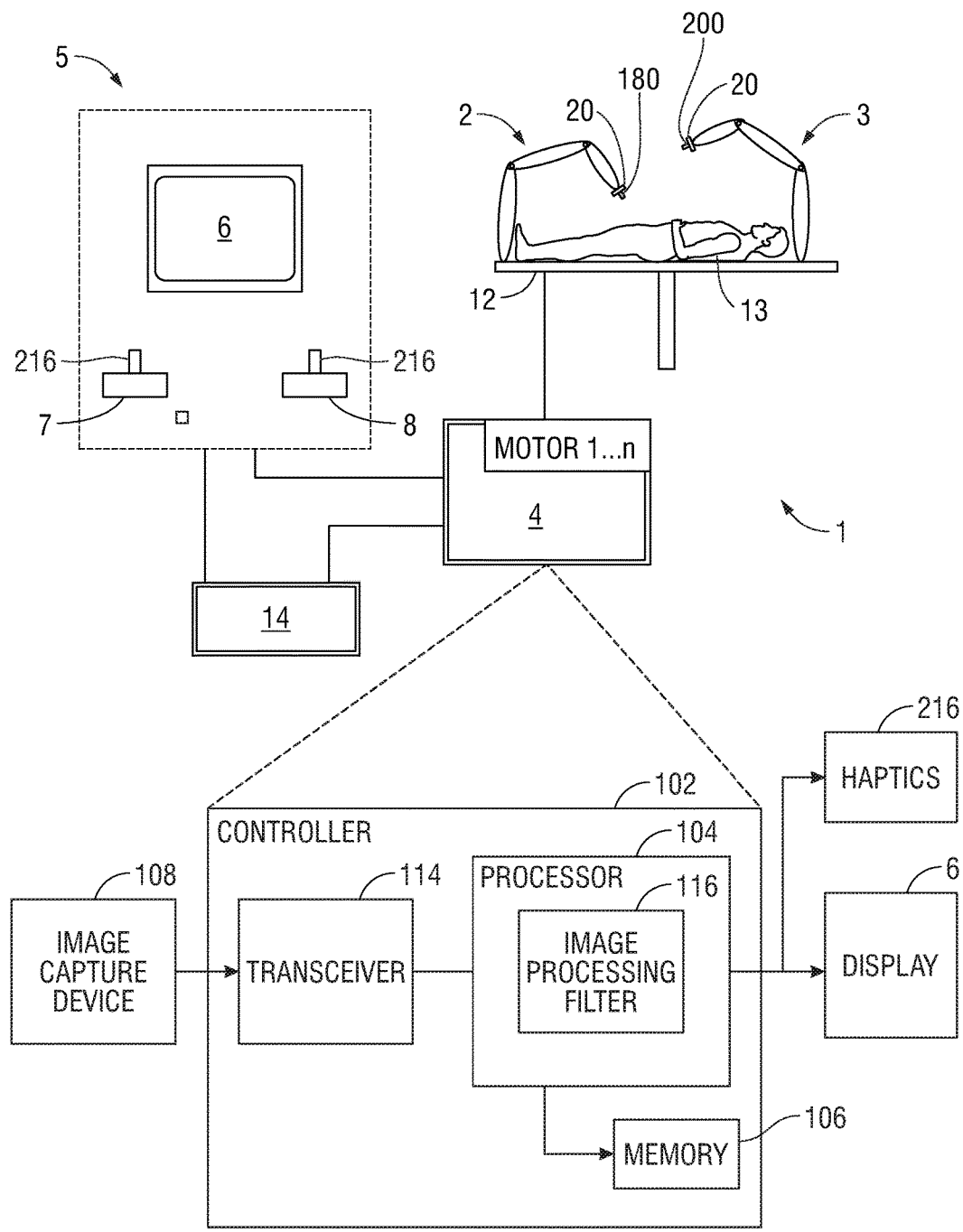
FIG. 8 is a system block diagram of a robotic surgical system.

The above-described embodiments may also be integrated into a robotic surgical system. FIG. 8 shows various components that may be included in a robotic surgical system 1, such as two or more robot arms 2, 3; a control device 4; and an operating console 5 coupled with control device 4. Operating console 5 may include a display device 6, which may be set up in particular to display three-dimensional images; and one or more manual input devices 7, 8, by means of which a person (not shown), for example a surgeon, is able to telemanipulate robot arms 2, 3 in a first operating mode.

The movement of input devices 7, 8 may be scaled so that a surgical instrument attached to a robot arm 2, 3 has a corresponding movement that is different (e.g. smaller or larger) than the movement of the input devices 7, 8. The scale factor or gearing ratio may be adjustable so that the clinician can control the resolution of the working ends of the surgical instrument.

Each of the robot arms 2, 3 may include a plurality of members, which are connected through joints, and a surgical assembly 20 to which may be attached, for example, a surgical instrument, such as, for example, an image capture device 108, such as an endoscope, or other surgical instrument having an end effector 200, in accordance with any of the embodiments disclosed herein. A distal end of surgical assembly 20 may be configured to support an image capture device 108 and/or other surgical instruments having end effectors 200, including, but not limited to a grasper, surgical stapler, a surgical cutter, a surgical stapler-cutter, a linear surgical stapler, a linear surgical stapler-cutter, a circular surgical stapler, a circular surgical stapler-cutter, a surgical clip applier, a surgical clip ligator, a surgical clamping device, a vessel expanding device, a lumen expanding device, a scalpel, a fluid delivery device or any other type of surgical instrument. Each of these surgical instruments may be configured for actuation and manipulation by the robot arms 2, 3 via force transmitting members. Force transmitting members may be variously configured, such as, for example, hypotubes, push rods, shafts, or tethers, and can transmit various forces, such as, for example, axial (i.e., pushing and pulling), rotary, and/or torque. An image capture device 108, such as an endoscope having a camera as an end effector 200 that articulates may include such force transmitting members. One or more of these force transmitting members may be configured to control the articulation of the camera.

Robot arms 2, 3 may be driven by electric drives that are connected to control device 4. Control device 4 (e.g., a computer) is set up to activate the drives, in particular by means of a computer program, in such a way that robot arms 2, 3, their surgical assemblies 20 and thus the end effector 200 execute a desired movement according to a movement defined by means of manual input devices 7, 8. Control device 4 may also be set up in such a way that it regulates the movement of robot arms 2, 3 and/or of the drives.

Control device 4 may also be communicatively coupled to other components of the surgical system 1, including, but not limited to, the surgical assemblies 20; display 6; input devices 7, 8; and surgical instruments coupled to robot arms 2, 3 such as image capture device 108 and instrument having an end effector 200. Control device 4 may also include or be coupled to controller 102. Controller 102 and/or control device 4 may include transceiver 114, which may be configured to receive still frame images or video from the image capture device 108 or data from sensor array 110. In some embodiments, the transceiver 114 may include an antenna to receive the still frame images, video, or data via a wireless communication protocol. The transceiver 114 may also receive the still frame images, video, or data via a wired connection. The still frame images, video, or data may be sent to processor 104. The processor 104 includes an image processing filter 116 that processes the received still frame images, video, or data to generate an augmented image or video. Processor 104 may include a buffer or memory 106 to store the images, video, or data being processed. The image processing filter 116 may be implemented using discrete components, software, or a combination thereof. The augmented image or video may be stored and/or sent to the display 6 or another output device.

In the surgical system 1, at least one image capture device 108 may be coupled to at least a first of the two or more robot arms 2, 3. The image capture device 108 may be configured to be inserted into the patient and capture an image of a region of interest inside the patient during a surgical procedure. The captured image may be displayed on the display 6.

Another surgical instrument having an end effector 200 configured to manipulate tissue in the region of interest during the surgical procedure may be coupled to at least a second of the two or more robot arms 2, 3.

The controller 102 may be configured to process image captured from image device 108 and apply at least one image processing filter 116 (e.g. filters 116A-116D in one or more of the different ways mentioned throughout the application) to the captured image to identify an imperceptible property of an object in the region of interest during the surgical procedure. The controller 102 may output the identified imperceptible property during the surgical procedure to the clinician. The imperceptible property may be outputted in different ways including to the display 6 where the imperceptible property may be shown to a clinician and/or by way of haptics so the clinician may feel the imperceptible property. When the imperceptible property is outputted to the display, the imperceptible property may be altered or transformed into a more clearly visible signal that may be overlayed onto a corresponding section of the captured image and shown to the clinician on the display.

Each of the instruments that may be attached to a robot arm 2, 3 may be equipped with a tool-type identifier, such as a quick response code, an identifier stored in a memory of the instrument, a particular circuit configuration associated with the tool-type, and so on. The surgical system 1 may include components or circuitry configured to receive and/or read the tool-type identifier from each instrument attached to a robot arm 2, 3. This information may then be used to select the specific image processing filters 116 that may be applied to the captured image.

The tool-type identifier information may be used to identify a surgical instrument attached to a robot arm 2,3 that is located with the field of view of the image capture device 108. For example, if a quick response code or other tool-type identifier is located on the end effector 200, shaft, or other component of the surgical instrument that appears within the field of view of the image device 108, then the captured image data may analyzed to identify the surgical instrument from the quick response code or other identifier identified from the image capture data.

In other instances, a surgical instrument that enters the field of view of the image capture device 108 may be identified based on a comparison of positional information about the image capture device 108 (and/or the robot arm 2 to which the image device 108 is attached) and an instrument attached to one of the other robot arms 3 (and/or the robot arm 3 to which the instrument is attached). Positional information may be obtained from one or more position sensors in each instrument or in the robot arms 2, 3. A transformation may be used to convert absolute positional information in different coordinate systems from different robot arms 2, 3 so that a relative position of the image capture device 108 on one robot arm 2 relative to the surgical instrument attached to another robot arm 3 may be obtained. The relative position information may be used to identify whether the surgical instrument attached to the other robot arm 3 is within the field of view of the image capture device 108.

In other instances, one or more cameras may be used to capture an image of one or more of the robot arms 2, 3. The image data from these cameras may be analyzed to identify the position of each of the robot arms 2, 3. This positional information may be analyzed to determine if the robot arm 3 to which the surgical instrument is attached is located within the field of view of the image capture device 108. Other systems and methods for determining whether a robot arm 3 to which a surgical instrument is attached is located within the field of view of the image capture device 108 may also be used.

If the positional information and/or the tool-type identifier indicate that a particular surgical instrument is within the field of view of the image capture device 108, then one or more of the image processing filters 116 may be automatically selected that correspond to the particular surgical instrument. For example, if an electro-cauterization surgical instrument is identified as being within the field of view of image capture device 108, then an image processing filter 116 showing an effectiveness of a vessel seal may be automatically selected. If the electro-cauterization instrument is then moved out of the field of view and a cutting instrument, such as a scalpel in moved into the field of view, then a different image processing filter 116 showing the location of large arteries may be automatically selected instead.

Different image processing filters 116 may be automatically selected depending on the task that is to be performed. For example, if a cutting tool is in the field of view and is being moved at a rate exceeding a predetermined threshold and/or a scaling factor of the input device 7, 8, is changed so that the surgical instrument moves faster, an image processing filters 116 showing the location of large arteries may be automatically selected. However, if the cutting tool is being moved a slower rate and/or activated to methodically cut and/or remove tissue, then an image processing filter 116 showing abnormal tissue may be used instead. The same analysis may applied to electro-cauterization tools—if the tool has not been activated within a predetermined period and/or is being moved at a rate exceeding a predetermined threshold then an image processing filter 116 showing the location of large arteries may be automatically selected. However, if the electro-cauterization tool is being moved a slower rate and/or activated within the predetermined period to methodically cut and/or remove tissue, then an image processing filter 116 showing an effectiveness of a vessel seal or other desired property may be used instead.

The input device 7, 8 may include haptics 216 to provide feedback to the clinician relating to the imperceptible property. For example, an output signal representative of a tissue parameter or condition, e.g., tissue resistance due to manipulation, cutting or otherwise treating, pressure by the instrument onto the tissue, tissue temperature, tissue impedance, and so on, may be generated and transmitted to the input device 7, 8 to provide haptic feedback to the clinician that varies based on the imperceptible property. Haptics 216 may provide the clinician with enhanced tactile feedback about imperceptible properties of objects that may improve patient safety. For example, haptics 216 may be implemented to provide feedback to the clinician when a surgical instrument moved by the input device 7, 8 comes within a predetermined distance of a large artery or other delicate tissue to prevent possible injury to the artery and/or delicate tissue. Haptics 216 may include vibratory motors, electroacitve polymers, piezoelectric devices, electrostatic devices, subsonic audi wave surface actuation devices, reverse-electrovibration, or any other device capable of providing a tactile feedback to a user. The input device 7, 8 may also include a variety of different actuators for delicate tissue manipulation or treatment further enhancing the clinician's ability to mimic actual operating conditions.

The embodiments disclosed herein are examples of the disclosure and may be embodied in various forms. Specific structural and functional details disclosed herein are not to be interpreted as limiting, but as a basis for the claims and as a representative basis for teaching one skilled in the art to variously employ the present disclosure in virtually any appropriately detailed structure. Like reference numerals may refer to similar or identical elements throughout the description of the figures.

The phrases "in an embodiment," "in embodiments," "in some embodiments," or "in other embodiments," which may each refer to one or more of the same or different embodiments in accordance with the present disclosure. A phrase in the form "A or B" means "(A), (B), or (A and B)". A phrase in the form "at least one of A, B, or C" means "(A), (B), (C), (A and B), (A and C), (B and C), or (A, B and C)". A clinician may refers to a clinician or any medical professional, such as a doctor, nurse, technician, medical assistant, or the like) performing a medical procedure.

The systems described herein may also utilize one or more controllers to receive various information and transform the received information to generate an output. The controller may include any type of computing device, computational circuit, or any type of processor or processing circuit capable of executing a series of instructions that are stored in a memory. The controller may include multiple processors and/or multicore central processing units (CPUs) and may include any type of processor, such as a microprocessor, digital signal processor, microcontroller, or the like. The controller may also include a memory to store data and/or algorithms to perform a series of instructions.

Any of the herein described methods, programs, algorithms or codes may be converted to, or expressed in, a programming language or computer program. A "Programming Language" and "Computer Program" includes any language used to specify instructions to a computer, and includes (but is not limited to) these languages and their derivatives: Assembler, Basic, Batch files, BCPL, C, C+, C++, Delphi, Fortran, Java, JavaScript, Machine code, operating system command languages, Pascal, Perl, PL1, scripting languages, Visual Basic, metalanguages which themselves specify programs, and all first, second, third, fourth, and fifth generation computer languages. Also included are database and other data schemas, and any other metalanguages. No distinction is made between languages which are interpreted, compiled, or use both compiled and interpreted approaches. No distinction is also made between compiled and source versions of a program. Thus, reference to a program, where the programming language could exist in more than one state (such as source, compiled, object, or linked) is a reference to any and all such states. Reference to a program may encompass the actual instructions and/or the intent of those instructions.

Any of the herein described methods, programs, algorithms or codes may be contained on one or more machine-readable media or memory. The term "memory" may include a mechanism that provides (e.g., stores and/or transmits) information in a form readable by a machine such a processor, computer, or a digital processing device. For example, a memory may include a read only memory (ROM), random access memory (RAM), magnetic disk storage media, optical storage media, flash memory devices, or any other volatile or non-volatile memory storage device. Code or instructions contained thereon can be represented by carrier wave signals, infrared signals, digital signals, and by other like signals.

It should be understood that the foregoing description is only illustrative of the present disclosure. Various alternatives and modifications can be devised by those skilled in the art without departing from the disclosure. For instance, any of the augmented images described herein can be combined into a single augmented image to be displayed to a clinician. Accordingly, the present disclosure is intended to embrace all such alternatives, modifications and variances. The embodiments described with reference to the attached drawing figs. are presented only to demonstrate certain examples of the disclosure. Other elements, steps, methods and techniques that are insubstantially different from those described above and/or in the appended claims are also intended to be within the scope of the disclosure.

What is claimed is:

1. An augmented reality surgical system for viewing an augmented image of a region of interest during a surgical procedure, the system comprising:
   an image capture device configured to be inserted into a patient and capture an image of the region of interest inside the patient during the surgical procedure;
   a controller configured to receive the image and apply at least one image processing filter to the image to generate the augmented image, the image processing filter including:
      a spatial decomposition filter configured to decompose the image into a plurality of spatial frequency bands;
      a temporal filter that is configured to be applied to the plurality of spatial frequency bands to generate a plurality of temporally filtered bands;
      an adder configured to add each band in the plurality of spatial frequency bands to a corresponding band in the plurality of temporally filtered bands to generate a plurality of augmented bands; and
      a reconstruction filter configured to generate the augmented image by collapsing the plurality of augmented bands; and
   a display configured to display the augmented image to a user during the surgical procedure.

2. The augmented reality surgical system of claim 1, wherein the image capture device captures a video having a plurality of image frames and the controller applies the at least one image processing filter to each image frame of the plurality of image frames.

3. The augmented reality surgical system of claim 1, wherein the temporal filter includes a bandpass filter.

4. The augmented reality surgical system of claim 3, wherein a bandpass frequency of the bandpass filter is set by a clinician.

5. The augmented reality surgical system of claim 1, wherein the temporal filter isolates at least one spatial frequency band from the plurality of spatial frequency bands to generate the plurality of temporally filtered bands.

6. The augmented reality surgical system of claim 1, wherein the plurality of temporally filtered bands are amplified by an amplifier before each band in the plurality of spatial frequency bands is added to the corresponding band in the plurality of temporally filtered bands to generate the plurality of augmented bands.

7. The augmented reality surgical system of claim 1, wherein the image processing filter uses an edge detection algorithm configured to highlight one or more edges in the image,
   wherein the one or more highlighted edges is added to the augmented image.

8. The augmented reality surgical system of claim 1, further comprising at least one hyper-spectral sensor configured to obtain a plurality of hyper-spectral images,
   wherein the image processing filter uses a hyper-spectral algorithm to combine the plurality of spectral images to generate a three dimensional hyper-spectral image cube that is added to the augmented image.

9. The augmented reality surgical system of claim 1, further comprising an infrared camera configured to capture at least one image,
   wherein the image processing filter generates an infrared image from the captured image, the infrared image is added to the augmented image.

10. A method for generating an augmented image of a region of interest during a surgical procedure, the method comprising:
    capturing at least one image of the region of interest using an image capture device;
    decomposing the at least one image to generate a plurality of spatial frequency bands;
    applying a temporal filter to the plurality of spatial frequency bands to generate a plurality of temporally filtered bands;
    adding each band in the plurality of spatial frequency bands to a corresponding band in the plurality of temporally filtered bands to generate a plurality of augmented bands;
    collapsing the plurality of augmented bands to generate the augmented image; and
    displaying the augmented image on a display.

11. The method of claim 10, further comprising isolating at least one spatial frequency band from the plurality of spatial frequency bands.

12. The method of claim 11, further comprising amplifying the temporally filtered bands before adding each band in the plurality of spatial frequency bands to a corresponding band in the plurality of temporally filtered bands to generate a plurality of augmented bands.

13. The method of claim 10, further comprising:
    applying an edge detection algorithm configured to highlight one or more edges in the image; and
    adding the one or more highlighted edges to the augmented image.

14. The method of claim 10, further comprising:
    obtaining a plurality of hyper-spectral images;
    combining the plurality of hyper-spectral images to generate a three dimensional hyper-spectral image cube; and adding the three dimensional hyper-spectral image cube to the augmented image.

15. The method of claim 10, further comprising:
obtaining an infrared image; and
adding the infrared image to the augmented image.

16. A non-transitory computer readable medium storing instructions that, when executed by a processing device, cause the processing device to:
decompose image data including an imperceptible property of an object;
generate a plurality of spatial frequency bands from the decomposed image data;
temporally filter the plurality of spatial frequency bands;
generate a plurality of temporally filtered bands;
add each of the spatial frequency bands to a corresponding band of the temporally filtered bands;
collapse the added bands;
generate an augmented image with improved perceptibility of the imperceptible property from the collapsing of the added bands; and
output the augmented image.

17. The non-transitory computer readable medium of claim 16, further comprising additional stored instructions that, when executed by a processing device, cause the processing device to isolate at least one spatial frequency band containing information about the imperceptible property from the plurality of spatial frequency bands.

18. The non-transitory computer readable medium of claim 17, further comprising additional stored instructions that, when executed by a processing device, cause the processing device to amplify the temporally filtered bands before adding each band in the plurality of spatial frequency bands to a corresponding band in the plurality of temporally filtered bands.

19. The non-transitory computer readable medium of claim 16, further comprising additional stored instructions that, when executed by a processing device, cause the processing device to:
apply an edge detection algorithm configured to highlight one or more edges in the image data, the one or more edges being the imperceptible property; and
add the one or more highlighted edges to the augmented image.

20. The non-transitory computer readable medium of claim 16, further comprising additional stored instructions that, when executed by a processing device, cause the processing device to:
obtain a plurality of hyper-spectral images;
combine the plurality of hyper-spectral images to generate a three dimensional hyper-spectral image cube; and
add the three dimensional hyper-spectral image cube to the augmented image.

* * * * *